(12) United States Patent
Miyazaki et al.

(10) Patent No.: US 9,987,368 B2
(45) Date of Patent: Jun. 5, 2018

(54) PHARMACEUTICAL COMPOSITION COMPRISING POLYPEPTIDE

(71) Applicant: SANTEN PHARMACEUTICAL CO., LTD., Osaka-shi, Osaka (JP)

(72) Inventors: Tatsuya Miyazaki, Shiga (JP); Kenji Masaki, Ikoma (JP); Komei Okabe, Ikoma (JP); Kazuhito Yamada, Ikoma (JP)

(73) Assignee: SANTEN PHARMACEUTICAL CO., LTD., Osaka-Shi, Osaka (JP)

( * ) Notice: Subject to any disclaimer, the term of this patent is extended or adjusted under 35 U.S.C. 154(b) by 0 days. days.

(21) Appl. No.: 15/558,893

(22) PCT Filed: Mar. 16, 2016

(86) PCT No.: PCT/JP2016/058359
§ 371 (c)(1),
(2) Date: Sep. 15, 2017

(87) PCT Pub. No.: WO2016/148201
PCT Pub. Date: Sep. 22, 2016

(65) Prior Publication Data
US 2018/0064818 A1    Mar. 8, 2018

(30) Foreign Application Priority Data

Mar. 17, 2015  (JP) ................ 2015-053757

(51) Int. Cl.
| | |
|---|---|
| *A61K 38/00* | (2006.01) |
| *A61K 47/42* | (2017.01) |
| *C07K 7/08* | (2006.01) |
| *A61K 47/22* | (2006.01) |
| *A61K 47/20* | (2006.01) |
| *A61K 45/00* | (2006.01) |
| *A61K 47/10* | (2017.01) |
| *A61K 31/095* | (2006.01) |
| *C08L 71/08* | (2006.01) |
| *C07C 317/04* | (2006.01) |
| *A61K 31/444* | (2006.01) |

(52) U.S. Cl.
CPC .............. *A61K 47/42* (2013.01); *A61K 45/00* (2013.01); *A61K 47/10* (2013.01); *A61K 47/20* (2013.01); *A61K 47/22* (2013.01); *C07K 7/08* (2013.01); *A61K 31/095* (2013.01); *A61K 31/444* (2013.01); *C07C 317/04* (2013.01); *C08L 71/08* (2013.01)

(58) Field of Classification Search
None
See application file for complete search history.

(56) References Cited

U.S. PATENT DOCUMENTS

| | | | |
|---|---|---|---|
| 2007/0149574 A1 | 6/2007 | Honda et al. | |
| 2012/0289462 A1 | 11/2012 | Shibata et al. | |
| 2015/0038428 A1 | 2/2015 | Hauser et al. | |
| 2016/0228420 A1 | 8/2016 | Murai et al. | |

FOREIGN PATENT DOCUMENTS

| | | |
|---|---|---|
| JP | 2006-096739 A | 4/2006 |
| JP | 2015-083565 A | 4/2015 |
| WO | WO 2013/126017 A1 | 8/2013 |
| WO | 2014/133027 A1 | 9/2014 |

OTHER PUBLICATIONS

International Search Report (PCT/ISA/210) dated May 24, 2016, by the Japanese Patent Office as the International Searching Authority for International Application No. PCT/JP2016/058359.

Written Opinion (PCT/ISA/237) dated May 24, 2016, by the Japanese Patent Office as the International Searching Authority for International Application No. PCT/JP2016/058359.

Maria-Lucia Briuglia et al., "Sustained and controlled release of lipophilic drugs from a self-assembling amphiphilic peptide hydrogel," International Journal of Pharmaceutics, 2014, pp. 103-111, vol. 474.

Jingping Liu et al., "Controlled release of paclitaxel from a self-assembling peptide hydrogel formed in situ and antitumor study in vitro," International Journal of Nanomedicine, 2011, pp. 2143-2153, vol. 6.

Asako Nishimura et al., "Controlled release of insulin from self-assembling nanofiber hydrogel, PuraMatrix™: Application for the subcutaneous injection in rats," European Journal of Pharmaceutical Sciences, 2012, pp. 1-7, vol. 45.

Extended Search Report issued by the European Patent Office in corresponding European Patent Application No. 16765030.8-1114 dated Apr. 6, 2018 (8 pages).

*Primary Examiner* — Jeanette M Lieb

(74) *Attorney, Agent, or Firm* — Buchanan, Ingersoll & Rooney PC

(57) ABSTRACT

Found out is a pharmaceutical composition that sustained-releases a drug for a long term after administration into the body. Provided is a pharmaceutical composition comprising a drug and a polypeptide represented by Ac-(Arg-Ala-Asp-Ala)$_4$-NH$_2$, and further containing an organic solvent selected from the group consisting of polyethylene glycol, dimethyl sulfoxide, glycofurol, and N-methylpyrrolidone.

20 Claims, No Drawings

```
SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Polypeptide sold as PuraMatrix (registered
      trademark)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 1

Arg Ala Asp Ala Arg Ala Asp Ala Arg Ala Asp Ala Arg Ala Asp Ala
1               5                   10                  15
```

PHARMACEUTICAL COMPOSITION COMPRISING POLYPEPTIDE

TECHNICAL FIELD

The present invention relates to a pharmaceutical composition comprising a drug, a polypeptide represented by Ac-(Arg-Ala-Asp-Ala)$_4$-NH$_2$, and a specific organic solvent, a sustained-release ability imparting agent for drug containing the polypeptide, and a specific organic solvent, and a method of imparting sustained-release ability to a drug. This application claims the benefit of priority of the prior Japanese Patent Application No. 2015-053757, filed on Mar. 17, 2015, the entire contents of which are incorporated herein by reference.

BACKGROUND ART

From the viewpoint of burdens of medication administration on patients, an invasive medication such as an intravitreal injection, for example, is desirably a medication which, after administration of a drug into the body, sustained-releases the drug from a site to which the drug is administered, and thereby produces a drug efficacy for a long term. As means for achieving this, hydrogel preparations utilizing self-assembling peptides have been reported.

Patent Literature 1 and Non-Patent Literature 1 disclose a sustained-release preparation for insulin as a water-soluble medication, the preparation using a polypeptide represented by Ac-(Arg-Ala-Asp-Ala)$_4$-CONH$_2$ (SEQ ID NO: 1) as a self-assembling peptide. In addition, Non-Patent Literature 2 discloses a sustained-release preparation using a polypeptide represented by Ac-(Arg-Ala-Asp-Ala)$_4$-CONH$_2$ and containing pindolol, quinine, and timolol maleate as drugs. Here, in the aforementioned literatures, the polypeptide represented by Ac-(Arg-Ala-Asp-Ala)$_4$-CONH$_2$ is PuraMatrix (registered trademark), and PuraMatrix (registered trademark) is also represented by Ac-(Arg-Ala-Asp-Ala)$_4$-NH$_2$. For this reason, PuraMatrix (registered trademark) is referred to as Ac-(Arg-Ala-Asp-Ala)$_4$-NH$_2$ (SEQ ID NO: 1) in the present specification.

However, the sustained-release preparations described in these literatures use only water as a solvent. None of these literatures discloses that an organic solvent selected from the group consisting of polyethylene glycol, dimethyl sulfoxide, glycofurol, and N-methylpyrrolidone is used as a solvent of a pharmaceutical composition comprising a drug and a polypeptide represented by Ac-(Arg-Ala-Asp-Ala)$_4$-NH$_2$, or states that the pharmaceutical composition is useful as a drug sustained-release preparation.

CITATION LIST

Patent Literature

Patent Literature 1: Specification of US Patent application Publication No. 2012/0289462

Non-Patent Literatures

Non-Patent Literature 1: Euro. J. Pharm. Sci., 45, 2012, 1-7
Non-Patent Literature 2: Int. J. Pharm., 474, 2014, 103-111

SUMMARY OF INVENTION

Technical Problem

An object of the present invention is to find out a pharmaceutical composition that sustained-releases a drug for a long term after administration into the body.

Solution to Problem

The present inventors earnestly studied gelatinizers for forming hydrogel, solvents for dissolving a drug, and the like in order to achieve the aforementioned object, and as a result found that a pharmaceutical composition in which a drug and a polypeptide represented by Ac-(Arg-Ala-Asp-Ala)$_4$-NH$_2$ are mixed with at least one organic solvent selected from the group consisting of polyethylene glycol, dimethyl sulfoxide, glycofurol, and N-methylpyrrolidone sustained-releases the drug, and thereby completed the present invention.

More specifically, the present invention relates to the followings.

[1] A pharmaceutical composition comprising a drug, a polypeptide represented by Ac-(Arg-Ala-Asp-Ala)$_4$-NH$_2$, and an organic solvent, in which the organic solvent is at least one organic solvent selected from the group consisting of polyethylene glycol, dimethyl sulfoxide, glycofurol, and N-methylpyrrolidone.

[2] The pharmaceutical composition according to the above [1], further containing water.

[3] The pharmaceutical composition according to the above [2], in which a volume ratio of the organic solvent to the water is 99:1 to 60:40.

[4] The pharmaceutical composition according to any one of the above [1] to [3], in which the organic solvent is polyethylene glycol, and the polyethylene glycol has a mean molecular weight within a range of 90 to 2200.

[5] The pharmaceutical composition according to any one of the above [1] to [3], in which the organic solvent is polyethylene glycol, and the polyethylene glycol is PEG 400.

[6] The pharmaceutical composition according to any one of the above [1] to [5], in which a content of the drug is 0.01 to 30% (w/v).

[7] The pharmaceutical composition according to any one of the above [1] to [6], in which a content of the polypeptide represented by Ac-(Arg-Ala-Asp-Ala)$_4$-NH$_2$ is 0.001 to 5% (w/v).

[8] The pharmaceutical composition according to any one of the above [1] to [7], in which a content of the organic solvent is 70 to 99.99% (w/w).

[9] The pharmaceutical composition according to any one of the above [1] to [8], in which the pharmaceutical composition consists substantially only of the drug, the polypeptide represented by Ac-(Arg-Ala-Asp-Ala)$_4$-NH$_2$, the polyethylene glycol, and the water.

[10] The pharmaceutical composition according to the above [1], in which the pharmaceutical composition consists substantially only of the drug, the polypeptide represented by Ac-(Arg-Ala-Asp-Ala)$_4$-NH$_2$, and the dimethyl sulfoxide.

[11] The pharmaceutical composition according to any one of the above [1] to [10], in which the drug is a compound or a salt thereof, the compound represented by formula (1):

(1)

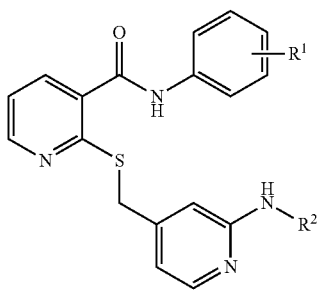

wherein

R¹ represents a hydrogen atom, a halogen atom, a hydroxyl group, a $C_{1-6}$ alkyl group, a $C_{1-6}$ alkyl group substituted with one or more halogen atoms, a $C_{1-6}$ alkoxy group, or $C_{1-6}$ alkoxy group substituted with one or more halogen atoms; and R² represents a hydrogen atom, $C_{1-6}$ alkyl group, a $C_{1-6}$ alkylcarbonyl group, or a $C_{1-6}$ alkylcarbonyl group substituted with one or more hydroxyl groups.

[12] The pharmaceutical composition according to any one of the above [1] to [10], in which the drug is 2-[[[2-[(hydroxyacetyl)amino]-4-pyridinyl]methyl]thio]-N-[4-(trifluoromethoxy)phenyl]-3-pyridinecarboxamide or a salt thereof.

[13] The pharmaceutical composition according to any one of the above [1] to [12], in which the pharmaceutical composition is for preventing or treating an eye disease.

[14] The pharmaceutical composition according to the above [13], in which the pharmaceutical composition is for intravitreal or intracameral administration.

[15] The pharmaceutical composition according to the above [13] or [14], in which the pharmaceutical composition is for sustained-release of the drug.

[16] A sustained-release ability imparting agent for drug containing: a polypeptide represented by Ac-(Arg-Ala-Asp-Ala)$_4$-NH$_2$; and an organic solvent, in which the organic solvent is at least one organic solvent selected from the group consisting of polyethylene glycol, dimethyl sulfoxide, glycofurol, and N-methylpyrrolidone.

[17] A method of imparting a sustained-release ability to a drug, the method including adding a polypeptide represented by Ac-(Arg-Ala-Asp-Ala)$_4$-NH$_2$ and an organic solvent to a drug, in which the organic solvent is at least one organic solvent selected from the group consisting of polyethylene glycol, dimethyl sulfoxide, glycofurol, and N-methylpyrrolidone.

It should be noted that any two or more of the structures [1] to [17] may be selected and combined as needed.

Advantageous Effects of Invention

The pharmaceutical composition of the present invention is one which dissolves the drug therein, and which forms a depot and sustained-releases the drug after administration into the body. Furthermore, the pharmaceutical composition of the present invention is sufficiently safe as a pharmaceutical product.

The sustained-release ability imparting agent in the present invention is suitable to impart a favorable sustained-release ability to a drug.

The method of imparting a sustained-release ability to a drug in the present invention is capable of imparting a favorable sustained-release ability to a drug.

DESCRIPTION OF EMBODIMENT

Hereinafter, the present invention will be described in detail.

<Polypeptide>

A polypeptide in the present invention is a polypeptide represented by Ac-(Arg-Ala-Asp-Ala)$_4$-NH$_2$ (SEQ ID NO: 1) (hereinafter also referred to as the polypeptide A) and is sold as PuraMatrix (registered trademark) by 3-D Matrix, Ltd. The C-terminal carboxyl group (COOH) is amidated (CONH$_2$).

A content of the polypeptide A is not particularly limited, but is preferably 0.001 to 5% (w/v), more preferably 0.005 to 3% (w/v), even more preferably 0.01 to 2% (w/v), particularly preferably 0.05 to 1% (w/v), and most preferably 0.1 to 0.5% (w/v). Note that "% (w/v)" means a mass (g) of a concerned ingredient (the polypeptide A herein) contained per 100 mL of a pharmaceutical composition in the present invention. Unless otherwise specified, the same applies below.

<Drug>

A drug in the present invention is not particularly limited, but is preferably a hydrophobic drug. The hydrophobic drug is a drug that tends not to be dissolved in water, and a hydrophobicity degree is expressed by an indicator such as a partition coefficient CLogP. CLogP is a calculated value of the logarithm of a 1-octanol/water partition coefficient, and the detailed explanation thereof is provided in Japanese Patent Application Publication No. 2009-298878 and so on. As the drug in the present invention, a hydrophobic drug specified as having a partition coefficient CLogP of 0.5 or more is preferable, a drug having a CLogP of 1 to 20, both inclusive, is more preferable, a drug having a CLogP of 1.5 to 15, both inclusive, is even more preferable, a drug having a CLogP of 2 to 12, both inclusive, is even further preferable, a compound having a CLogP of 2.2 to 9, both inclusive, is particularly more preferable, and a compound having a CLogP of 2.5 to 8, both inclusive, is most preferable. Specific examples of the drug in the present invention include: tyrosine kinase inhibitors such as Tafetinib, SIM-817378, ACTB-1003, Chiauranib, CT-53608, Cinnamon, chim4G8-SDIE, CEP-5214, IMC-1C11, CEP-7055, 3-[5-[2-[N-(2-Methoxyethyl)-N-methylamino]ethoxy]-1H-indol-2-yl]quinolin-2(1H)-one, hF4-3C5, ZK-CDK, IMC-EB10, LS-104, CYC-116, OSI-930, PF-337210, JNJ-26483327, SSR-106462, R-1530, PRS-050, TG-02, SC-71710, SB-1578, AMG-191, AMG-820, Sulfatinib, Lucitanib hydrochloride, JNJ-28312141, Ilorasertib, PLX-5622, ARRY-382, TAS-115, Tanibirumab, Henatinib, LY-2457546, PLX-7486, FPA-008, NVP-AEE-788, cgi-1842, RAF-265, MK-2461, SG-00529, Rebastinib, Golvatinib, Roniciclib, BVT-II, X-82, XV-615, KD-020, Lestaurtinib, Delphinidin, Semaxanib, Vatalanib, OSI-632, Telatinib, Alacizumab pegol, ATN-224, Tivozanib, XL-999, Icrucumab, Foretinib, Crenolanib besylate, R-406, Brivanib, Pegdinetanib, TG-100572, Olaratumab, Fostamatinib disodium, BMS-690514, AT-9283, MGCD-265, Quizartinib, ENMD-981693, Famitinib, Anlotinib, Tovetumab, PLX-3397, Fruquintinib, (−)-Epigallocatechin, Midostaurin, NSC-706456, Orantinib, Cediranib, Dovitinib, XL-647, Motesanib, Linifanib, Brivanib, Cediranib, Apatinib, Fedratinib, Pacritinib, Ramucirumab, Intedanib, Masitinib, Elemene, Dihydroartemisinin, WS-1442, Itranazole, Leflunomide, Dihydroartemisinin, Imatinib, Sorafenib, Sunitinib, Dasatinib, Pazopanib, Vandetanib, Axitinib, Regorafenib, and Cabozantiniband Ponatinib; steroids such as hydrocortisone, triamcinolone, fluocinolone, dexamethasone, and betamethasone; prostaglandin derivatives such as isopropyl unoprostone, latanoprost, bimatoprost, and travoprost; immunosuppressants such as cyclosporin, sirolimus, and FK506; anti-allergic agents such as azelastine; non-steroidal anti-inflammatory drugs such as indomethacin, bromfenac, and diclofenac; angiogenesis inhibitors such as pazopanib, SU5416, balatinib, ranibizumab, and bevacizumab; circulation improving drugs such as nicardipine and nitrendipine; antioxidants such as vitamin E; carbonic anhydrase inhibitors such as acetazolamide and brinzolamide; β receptor blockers such as timolol and carteolol; visual cycle modulators such as vitamin A derivatives; trophic factors such as ciliary body trophic factor (CNTF) and brain-derived neurotrophic factor (BDNF); growth factors such as nerve growth factor (NGF) and stem cell growth factor (HGF); aptamers such as pegaptanib; various antisense nucleic acids; nucleic acid drugs such as siRNA; antibody/peptide preparations such as lucentis and IgG; VEGF inhibitors described in Japanese Patent Application Publication Nos. 2006-96739, 2011-37844, 2005-232149, 2006-273851, 2006-306861; 2008-266294, and so on; compounds having glucocorticoid receptor binding activity described in Japanese Patent Application Publication Nos. 2007-230993, 2008-074829, 2008-143889, 2008-143890, 2008-143891, 2009-007344, 2009-084274, and so on; selective glucocorticoid receptor agonists such as RU24858; anticancer drugs such as fluorouracil; janus kinase inhibitors such as tofacitinib; protein kinase inhibitors such as ruboxistaurin mesylate; and others.

In particular, it is preferable to use, as a drug in the present invention, a compound or a salt thereof, the compound represented by formula (1):

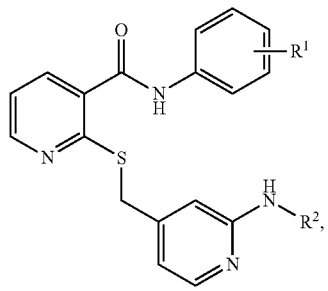

(1)

wherein

R$^1$ represents a hydrogen atom, a halogen atom, a hydroxyl group, a C$_{1-6}$ alkyl group, a C$_{1-6}$ alkyl group substituted with one or more halogen atoms, a C$_{1-6}$ alkoxy group, or a C$_{1-6}$ alkoxy group substituted with one or more halogen atoms; and R$^2$ represents a hydrogen atom, a C$_{1-6}$ alkyl group, a C$_{1-6}$ alkylcarbonyl group, or a C$_{1-6}$ alkylcarbonyl group substituted with one or more hydroxyl groups. A more preferable drug is a compound of the aforementioned formula (1) or a salt thereof, wherein R$^1$ represents a C$_{1-6}$ alkoxy group or a C$_{1-6}$ alkoxy group substituted with one or more halogen atoms, and R$^2$ represents a C$_{1-6}$ alkylcarbonyl group or a C$_{1-6}$ alkylcarbonyl group substituted with one or more hydroxyl groups. An even more preferable drug is a compound of the aforementioned formula (1) or a salt thereof, wherein R$^1$ represents a C$_{1-6}$ alkoxy group substituted with one or more halogen atoms, and R$^2$ represents a C$_{1-6}$ alkylcarbonyl group substituted with one or more hydroxyl groups.

Here, the "halogen atom" indicates fluorine, chlorine, bromine, or iodine.

The "C$_{1-6}$ alkyl group" indicates a linear or branched alkyl group having 1 to 6 carbon atoms, and is preferably a linear or branched alkyl group having 1 to 4 carbon atoms. Specific examples thereof include a methyl group, an ethyl group, an n-propyl group, an n-butyl group, an n-pentyl group, an n-hexyl group, an isopropyl group, an isobutyl group, a sec-butyl group, a tert-butyl group, an isopentyl group, and so on.

The "C$_{1-6}$ alkoxy group" indicates a group in which a hydrogen atom in a hydroxyl group is substituted with the C$_{1-6}$ alkyl group. Specific examples thereof include a methoxy group, an ethoxy group, an n-propoxy group, an n-butoxy group, an n-pentoxy group, an n-hexyloxy group, an isopropoxy group, an isobutoxy group, a sec-butoxy group, a tert-butoxy group, an isopentyloxy group, and so on.

The "C$_{1-6}$ alkylcarbonyl group" indicates a group in which a hydrogen atom in a formyl group is substituted with the C$_{1-6}$ alkyl group. Specific examples thereof include a methylcarbonyl group (acetyl group), an ethylcarbonyl group, an n-propylcarbonyl group, an n-butylcarbonyl group, an n-pentylcarbonyl group, an n-hexylcarbonyl group, an isopropylcarbonyl group, an isobutylcarbonyl group, a sec-butylcarbonyl group, a tert-butylcarbonyl group, an isopentylcarbonyl group, and so on.

The expression "substituted with one or more halogen atoms" indicates that the C$_{1-6}$ alkyl group in which one up to a maximum number of substitutable positions are substituted with a halogen atom(s). The halogen atoms may be the same as or different from each other. As the number of halogen atoms, 2 or 3 is preferable, or 3 is preferable in particular.

The expression "substituted with one or more hydroxyl groups" indicates that the C$_{1-6}$ alkyl group in which one up to a maximum number of substitutable positions are substituted with a hydroxyl group(s). As the number of hydroxyl groups, 1 or 2 is preferable, or 1 is preferable in particular.

A particularly preferable specific example of the drug in the present invention is 2-[[[2-[(hydroxyacetyl)amino]-4-pyridinyl]methyl]thio]-N-[4-(trifluoromethoxy)phenyl]-3-pyridinecarboxamide represented by formula (2):

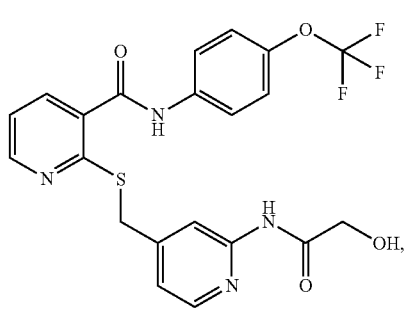

(2)

or a salt thereof. The specification of US Patent Application Publication No. 2007/0149574 discloses that the compound represented by the formula (2) and the like demonstrated a cell proliferation inhibitory action in a test using a VEGF-induced HUVEC proliferation evaluation system, demonstrated a tumor growth inhibitory action in a test using cancer models in mice, demonstrated a paw edema inhibitory action in a test using adjuvant arthritis models in rats, and demonstrated a choroidal neovascularization inhibitory action in a test using choroidal neovascularization models in rats. Further, it is also stated that the compound represented by the formula (2) is useful as medicines owing to these pharmacological actions, and is expected as preventive or therapeutic agents for diseases such as cancer, rheumatoid arthritis, age-related macular degeneration, diabetic retinopathy, and diabetic macular edema, in particular.

Also, the specification of US Patent Application Publication No. 2012/0116088 describes a benzenesulfonate of the compound represented by the formula (2), a crystal of the same, a crystal polymorph thereof, and production methods thereof, and states that the benzenesulfonate of the compound represented by the formula (2) is excellent in storage stability and causes no mineral deposition in the stomach even after repeated oral administration.

The compound represented by the formula (2) or a salt thereof contained in the pharmaceutical composition of the present invention can be manufactured according to a usual method in this technical field such as the method described in the specification of US Patent Application Publication No. 2007/0149574.

The drugs in the present invention also include derivatives such as esters and amides. A specific example of the esters is an ester in which a hydroxyl group in the drug is condensed with a carboxylic acid such as an acetic acid, a propionic acid, an isopropionic acid, a butyric acid, an isobutyric acid, or a pivalic acid. A Specific example of the amides is an amide in which an amino group in the drug is condensed with a carboxylic acid such as an acetic acid, a propionic acid, an isopropionic acid, a butyric acid, an isobutyric acid, or a pivalic acid.

In addition, the drug in the present invention may be in the form of a hydrate or a solvate.

In the case where geometric isomers, tautomers or optical isomers are present for the drugs in the present invention, these isomers are also included in the scope of the present invention.

Further, in the case where a crystal polymorph is present for the drug in the present invention, the crystal polymorph is also included in the scope of the present invention.

The drug in the present invention may be a salt, and be any pharmaceutically acceptable salt not particularly limited. As the salt, there are a salt with inorganic acid, a salt with organic acid, a quaternary ammonium salt, a salt with halogen ion, a salt with alkali metal, a salt with alkaline earth metal, a metal salt, a salt with organic amine, and so on. As a salt with inorganic acid, there is a salt with hydrochloric acid, hydrobromic acid, hydriodic acid, nitric acid, sulfuric acid, phosphoric acid, or the like. As a salt with organic acid, there is a salt with acetic acid, oxalic acid, fumaric acid, malein acid, succinic acid, malic acid, citric acid, tartaric acid, adipic acid, gluconic acid, glucoheptonic acid, glucuronic acid, terephthalic acid, methanesulfonic acid, alanine, lactic acid, hippuric acid, 1,2-ethanedisulfonic acid, isethionic acid, lactobionic acid, oleic acid, gallic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, sulfosalicylic acid, or the like. As a quaternary ammonium salt, there is a salt with methyl bromide, methyl iodide, or the like. As a salt with halogen ion, there is a salt with chloride ion, bromide ion, iodide ion, or the like. As a salt with alkali metal, there is a salt with lithium, sodium, potassium, or the like. As a salt with alkaline earth metal, there is a salt with calcium, magnesium, or the like. As a metal salt, there is a salt with iron, zinc, or the like. As a salt with organic amine, there is a salt with triethylenediamine, 2-aminoethanol, 2,2-iminobis (ethanol), 1-deoxy-1-(methylamino)-2-d-sorbitol, 2-amino-2-(hydroxymethyl)-1, 3-propanediol, procaine, n,n-bis (phenylmethyl)-1,2-ethanediamine, or the like.

A content of the drug in the present invention is not particularly limited as long as the drug is contained in an amount sufficient to produce a desired drug efficacy. However, the content of the drug is preferably 0.01 to 30% (w/v), more preferably 0.1 to 25% (w/v), even more preferably 0.5 to 20% (w/v), still even more preferably 1 to 15% (w/v), particularly preferably 1 to 12% (w/v), or most preferably 1% (w/v), 1.5% (w/v), 2% (w/v), 2.5% (w/v), 3% (w/v), 3.5% (w/v), 4% (w/v), 5% (w/v), 6% (w/v), 7% (w/v), 8% (w/v), 9% (w/v), 10% (w/v), 11% (w/v), or 12% (w/v).

<Organic Solvent>

The organic solvent in the present invention is selected from the group consisting of polyethylene glycol (PEG), dimethyl sulfoxide, glycofurol, and N-methylpyrrolidone.

Polyethylene glycol (PEG) as the aforementioned organic solvent is a polyether obtained by polymerization of ethylene glycol, and is represented by chemical formula $HO(CH_2CH_2O)_nH$, where n represents the number of repeating units.

A mean molecular weight of polyethylene glycol as the aforementioned organic solvent is 90 to 2200 preferably, 100 to 2000 more preferably, 100 to 1500 even more preferably, 100 to 1000 still even more preferably, 200 to 800 particularly preferably, 300 to 660 further particularly preferably, 400 to 600 even further particularly preferably, 400 and 600 still even further particularly preferably, or 400 most preferably. Specific examples of polyethylene glycol include PEG 100, PEG 200, PEG 300, PEG 400, PEG 600, PEG 800, PEG 1000, and the like.

Dimethyl sulfoxide (DMSO) as the aforementioned organic solvent is a compound represented by chemical formula $CH_3SOCH_3$.

Glycofurol as the aforementioned organic solvent is a compound represented by the following formula (3):

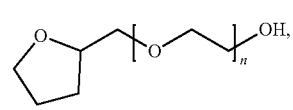

(3)

wherein n represents the number of repeating units, and is 1 to 20 preferably, 1 to 10 more preferably, 1 to 6 even more preferably, 1 to 4 particularly preferably, or 1 to 2 most preferably.

N-methylpyrrolidone as the aforementioned organic solvent is a compound containing tetrahydrofuran and polyethylene glycol and represented by the following formula (4):

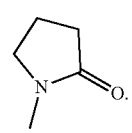

(4)

In addition to the aforementioned organic solvent selected from the group consisting of polyethylene glycol, dimethyl sulfoxide, glycofurol, and N-methylpyrrolidone, the pharmaceutical composition in the present invention may further contain a solvent usable as an additive for a pharmaceutical product, such as water, ethanol, and N,N-dimethylacetamide. It is particularly preferable to contain water from the viewpoint of dissolving the polypeptide A.

If the pharmaceutical composition in the present invention contains water, a volume ratio of the organic solvent selected from the group consisting of polyethylene glycol, dimethyl sulfoxide, glycofurol and N-methylpyrrolidone (polyethylene glycol is particularly preferable) to water is not particularly limited, but is 99:1 to 60:40 preferably, 97:3 to 70:30 more preferably, 95:5 to 75:25 even more preferably, or 90:10 to 80:20 most preferably.

A total content of the solvent in the pharmaceutical composition in the present invention is not particularly limited, but a value at % by mass of the solvent with respect to 100% by mass of the pharmaceutical composition in the present invention is 70 to 99.99% (w/w) preferably, 80 to 99.95% (w/w) more preferably, 85 to 99.9% (w/w) even more preferably, 90 to 99.5% (w/w) particularly preferably, or 92 to 99% (w/w) most preferably.

<Additive>

The pharmaceutical composition in the present invention may use an additive as needed, and any of surfactants, buffering agents, tonicity agents, stabilizers, preservatives, antioxidants, high molecular weight polymers, and so on may be added as the additive.

As a surfactant usable as the aforementioned additive, for example, a cationic surfactant, an anionic surfactant, or a nonionic surfactant may be blended. Examples of the anionic surfactant include phospholipids and the like, and the phospholipids include lecithin and the like. Examples of the cationic surfactant include an alkylamine salt, an alkylamine polyoxyethylene adduct, a fatty acid triethanolamine monoester salt, an acylaminoethyldiethylamine salt, a fatty acid polyamine condensate, an alkyltrimethylammonium salt, a dialkyldimethylammonium salt, an alkyldimethylbenzylammonium salt, an alkylpyridinium salt, an acylaminoalkyl type ammonium salt, an acylaminoalkylpyridinium salt, a diacyloxyethylammonium salt, an alkylimidazoline, a 1-acylaminoethyl-2-alkylimidazoline, a 1-hydroxylethyl-2-alkylimidazoline, and so on. As the alkyldimethylbenzylammonium salt, there are a benzalkonium chloride, a cetarconium chloride, and the like. Examples of the nonionic surfactant include a polyoxyethylene fatty acid ester, a polyoxyethylene sorbitan fatty acid ester, a polyoxyethylene hardened castor oil, a polyoxyethylene castor oil, a polyoxyethylene polyoxypropylene glycol, a sucrose fatty acid ester, vitamin E TPGS (tocopherol polyethylene glycol 1000 succinate, CAS 9002-96-4), and so on.

As the polyoxyethylene fatty acid ester, there are polyoxyl 40 stearate and so on.

As the polyoxyethylene sorbitan fatty acid ester, there are polysorbate 80, polysorbate 65, polysorbate 60, polysorbate 40, polysorbate 20, polyoxyethylene sorbitan monolaurate, polyoxyethylene sorbitan trioleate, and so on.

As the polyoxyethylene hardened castor oil, it is possible to use various kinds of polyoxyethylene hardened castor oils which are different in the number of repeating ethylene oxide units. The number of repeating ethylene oxide units is 10 to 100 preferably, 20 to 80 more preferably, 40 to 70 particularly preferably, or 60 most preferably. Specific examples of the polyoxyethylene hardened castor oil include polyoxyethylene hardened castor oil 10, polyoxyethylene hardened castor oil 40, polyoxyethylene hardened castor oil 50, polyoxyethylene hardened castor oil 60, and so on.

As the polyoxyethylene castor oil, it is possible to use various kinds of polyoxyethylene castor oils which are different in the number of repeating ethylene oxide units. The number of repeating ethylene oxide units is 5 to 100 preferably, 20 to 50 more preferably, 30 to 40 particularly preferably, or 35 most preferably. Specific examples of the polyoxyethylene castor oil include polyoxyl 5 castor oil, polyoxyl 9 castor oil, polyoxyl 15 castor oil, polyoxyl 35 castor oil, polyoxyl 40 castor oil, and so on.

As the polyoxyethylene polyoxypropylene glycol, there are polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol, polyoxyethylene (20) polyoxypropylene (20) glycol, and so on.

As the sucrose fatty acid ester, there are sucrose stearate and so on.

If the pharmaceutical composition in the present invention is blended with a surfactant, a content of the surfactant may be appropriately adjusted depending on a surfactant type or the like, but is 0.001 to 10% (w/v) preferably, 0.01 to 5% (w/v) more preferably, 0.05 to 3% (w/v) even more preferably, or 0.1 to 2% (w/v) most preferably.

As a buffering agent usable as the aforementioned additive, there are phosphoric acid or phosphate, boric acid or borate, citric acid or citrate, acetic acid or acetate, carbonic acid or carbonate, tartaric acid or tartrate, ε-aminocaproic acid, trometamol, and so on. As the phosphate, there are sodium phosphate, sodium dihydrogenphosphate, disodium hydrogen phosphate, potassium phosphate, potassium dihydrogenphosphate, dipotassium hydrogen phosphate, and so on. As the borate, there are borax, sodium borate, potassium borate, and so on. As the citrate, there are sodium citrate, disodium citrate, and so on. As the acetate, there are sodium acetate, potassium acetate, and so on. As the carbonate, there are sodium carbonate, sodium hydrogen carbonate, and so on. As the tartrate, there are sodium tartrate, potassium tartrate, and so on.

If the pharmaceutical composition in the present invention is blended with a buffering agent, a content of the buffering agent may be appropriately adjusted depending on a buffering agent type or the like, but is 0.001 to 10% (w/v) preferably, 0.01 to 5% (w/v) more preferably, 0.05 to 3% (w/v) even more preferably, or 0.1 to 2% (w/v) most preferably.

As a tonicity agent usable as the aforementioned additive, there are an ionic tonicity agent, a nonionic tonicity agent, and so on. As the ionic tonicity agent, there are sodium chloride, potassium chloride, calcium chloride, magnesium chloride, and so on. As the nonionic tonicity agent, there are glycerin, propylene glycol, sorbitol, mannitol, trehalose, sucrose, glucose, and so on.

If the pharmaceutical composition in the present invention is blended with a tonicity agent, a content of the tonicity agent may be appropriately adjusted depending on a tonicity agent type or the like, but is 0.001 to 10% (w/v) preferably, 0.01 to 5% (w/v) more preferably, 0.05 to 3% (w/v) even more preferably, or 0.1 to 2% (w/v) most preferably.

As a stabilizer usable as the aforementioned additive, there are edetic acid, sodium edetate, sodium citrate, and so on.

If the pharmaceutical composition in the present invention is blended with a stabilizer, a content of the stabilizer may be appropriately adjusted depending on a stabilizer type or the like, but is 0.001 to 10% (w/v) preferably, 0.01 to 5% (w/v) more preferably, 0.05 to 3% (w/v) even more preferably, or 0.1 to 2% (w/v) most preferably.

As a preservative usable as the aforementioned additive, there are benzalkonium chloride, benzalkonium bromide, benzethonium chloride, sorbic acid, potassium sorbate, methyl parahydroxybenzoate, propyl parahydroxybenzoate, chlorobutanol, and so on.

If the pharmaceutical composition in the present invention is blended with a preservative, a content of the preservative may be appropriately adjusted depending on a preservative type or the like, but is 0.0001 to 10% (w/v) preferably, 0.001 to 5% (w/v) more preferably, 0.005 to 3% (w/v) even more preferably, or 0.01 to 2% (w/v) most preferably.

As an antioxidant usable as the aforementioned additive, there are ascorbic acid, ascorbic acid derivatives such as ascorbyl palmitate, tocopherol, dibutylhydroxytoluene, butylhydroxyanisole, sodium erythorbate, propyl gallate, sodium sulfite, and so on.

If the pharmaceutical composition in the present invention is blended with an antioxidant, a content of the antioxidant may be appropriately adjusted depending on an antioxidant type or the like, but is 0.001 to 10% (w/v) preferably, 0.01 to 5% (w/v) more preferably, 0.05 to 3% (w/v) even more preferably, or 0.1 to 2% (w/v) most preferably.

As a high molecular weight polymer usable as the aforementioned additive, there are methylcellulose, ethylcellulose, hydroxymethylcellulose, hydroxyethyl cellulose, hydroxypropyl cellulose, hydroxyethylmethyl cellulose, hydroxypropylmethyl cellulose, carboxymethyl cellulose, sodium carboxymethyl cellulose, hydroxypropylmethyl cellulose acetate succinate, hydroxypropylmethyl cellulose phthalate, carboxymethylethyl cellulose, cellulose acetate phthalate, polyvinylpyrrolidone, polyvinyl alcohol, carboxyvinyl polymer, and so on.

If the pharmaceutical composition in the present invention is blended with a high molecular weight polymer, a content of the high molecular weight polymer may be appropriately adjusted depending on a high molecular weight polymer type or the like, but is 0.001 to 10% (w/v) preferably, 0.01 to 5% (w/v) more preferably, 0.05 to 3% (w/v) even more preferably, or 0.1 to 2% (w/v) most preferably.

A content of each additive usable as the aforementioned additive may be appropriately adjusted depending on an additive type or the like, but a total content thereof is 0.0001 to 30% (w/v) preferably, 0.001 to 25% (w/v) more preferably, 0.01 to 20% (w/v) even more preferably, 0.1 to 15% (w/v) particularly preferably, or 1 to 10% (w/v) most preferably.

A specific preferable embodiment of the pharmaceutical composition in the present invention is a pharmaceutical composition consisting substantially only of a drug, a polypeptide represented by Ac-(Arg-Ala-Asp-Ala)$_4$-NH$_2$, polyethylene glycol, and water.

A specific preferable embodiment of the pharmaceutical composition in the present invention is a pharmaceutical composition consisting substantially only of a compound represented by the formula (1) or a salt thereof, a polypeptide represented by Ac-(Arg-Ala-Asp-Ala)$_4$-NH$_2$, polyethylene glycol, and water.

A specific preferable embodiment of the pharmaceutical composition in the present invention is a pharmaceutical composition consisting substantially only of a compound represented by the formula (2) or a salt thereof, a polypeptide represented by Ac-(Arg-Ala-Asp-Ala)$_4$-NH$_2$, polyethylene glycol, and water.

A specific preferable embodiment of the pharmaceutical composition in the present invention is a pharmaceutical composition consisting substantially only of a drug, a polypeptide represented by Ac-(Arg-Ala-Asp-Ala)$_4$-NH$_2$, and dimethyl sulfoxide.

A specific preferable embodiment of the pharmaceutical composition in the present invention is a pharmaceutical composition consisting substantially only of a compound represented by the formula (1) or a salt thereof, a polypeptide represented by Ac-(Arg-Ala-Asp-Ala)$_4$-NH$_2$, and dimethyl sulfoxide.

A specific preferable embodiment of the pharmaceutical composition in the present invention is a pharmaceutical composition consisting substantially only of a compound represented by the formula (2) or a salt thereof, a polypeptide represented by Ac-(Arg-Ala-Asp-Ala)$_4$-NH$_2$, and dimethyl sulfoxide.

The pharmaceutical composition in the present invention may be administered orally or parenterally. The dosage form of the pharmaceutical composition in the present invention is not particularly limited as long as the pharmaceutical composition can be used as a pharmaceutical product. A dosage form example for an oral preparation is a liquid preparation, for example, whereas dosage form examples for parenteral preparations include an injection, an infusion, a nasal drop, an ear drop, an eye drop and the like. Here, ophthalmic injections and eye drops are preferable, ophthalmic injections are more preferable, or injections for intravitreal administration, intracameral administration and subconjunctival administration are the most preferable. These preparations can be manufactured according to any of usual methods in the technical field concerned.

The pharmaceutical composition in the present invention may be appropriately administered depending on the dosage form thereof. For example, in the case of an ophthalmic injection, the pharmaceutical composition can be administered into the vitreous body, in the vicinity of the posterior sclera, around the orbit, or between the sclera and the conjunctiva. In the case of administering the ophthalmic injection intravitreally or intracamerally, a dosage of the ophthalmic injection is not particularly limited as long as the dosage is sufficient to produce a desired drug efficacy, but the dosage per administration is preferably 1 to 100 µL, more preferably 5 to 70 µL, even more preferably 10 to 60 µL, particularly preferably 20 to 50 µL, or most preferably 10 µL, 20 µL, 25 µL, 30 µL, 35 µL, 40 µL, 45 µL or 50 µL. A dosage of the drug is preferably 0.001 to 30 mg/eye, more preferably 0.01 to 10 mg/eye, even more preferably 0.1 to 5 mg/eye, particularly preferably 0.2 to 1.6 mg/eye, or most preferably 0.2 mg/eye, 0.3 mg/eye, 0.4 mg/eye, 0.5 mg/eye, 0.6 mg/eye, 0.7 mg/eye, 0.8 mg/eye, 1 mg/eye, 1.2 mg/eye, 1.4 mg/eye or 1.6 mg/eye.

In the case of consecutively administering the pharmaceutical composition in the present invention into a vitreous or anterior chamber, an administration interval thereof is not particularly limited as long as the administrations at the intervals are sufficient to produce a desired drug efficacy. However, a preferable interval is within a range of once a week to once every three years. A more preferable interval is once a week, once every two weeks, once a month, once every two months, once every three months, once every four months, once every five months, once every six months, once a year, once every two years, or once every three years, and the most preferable interval is once every two months, once every three months, once every four months, once every five months, once every six months or once a year. Then, the administration interval can be appropriately changed depending on the kind of the drug, the sustained-release ability of the drug, symptoms of a patient, and so on.

The composition in the present invention is useful as a pharmaceutical medicine, and is particularly useful to prevent or treat eye diseases. Specific diseases which may be prevented and treated by the composition in the present invention include age-related macular degeneration, diabetic retinopathy, retinopathy of prematurity, retinal vein occlusion, retinal artery occlusion, polypoid choroidal angiopathy, retinal angiomatous proliferation, myopic choroidal neovascularization, diabetic macular edema, ocular tumor, radiation retinopathy, iris rubeosis, neovascular glaucoma, proliferative vitreoretinopathy (PVR), primary open-angle glaucoma, secondary open-angle glaucoma, normal tension glaucoma, hypersecretion glaucoma, primary angle-closure glaucoma, secondary angle-closure glaucoma, plateau iris glaucoma, mixed glaucoma, developmental glaucoma, steroid-induced glaucoma, exfoliation glaucoma, amyloidotic glaucoma, neovascular glaucoma, malignant glaucoma, capsular glaucoma, plateau iris syndrome, ocular hypertension, and so forth. It is more preferable to prevent or treat diseases such as age-related macular degeneration, diabetic retinopathy, primary open-angle glaucoma, normal tension glaucoma, primary angle-closure glaucoma, and ocular hypertension.

The pharmaceutical composition in the present invention has a sustained-release ability and is capable of gradually releasing an administered drug of the present invention into the body, that is, what is termed as extended-release of a drug. The sustained-release ability can be evaluated by measuring a release rate of the drug over time, for example. The release rate can be obtained in accordance with the following formula.

Release Rate (%)=[Amount of Drug Released (mass)]/[Initial Amount of Drug (Dosage) (mass)]×100

As for the release rate, a release rate after 1 day since administration, for example, is preferably 60% or less, more preferably 1 to 50%, or even more preferably 1 to 45%. In addition, a release rate after 6 days is preferably 97% or less, more preferably 5 to 95%, or even more preferably 10 to 90%.

When administrated into the body, the pharmaceutical composition in the present invention and/or a sustained-release ability imparting agent for drug to be described later is deposited in a mass, in other words, generates a "depot", and allows the drug contained in the pharmaceutical composition or the like to be slowly released from the depot, so that the aforementioned sustained-release ability can be attained.

<Sustained-Release Ability Imparting Agent for Drug>

A sustained-release ability imparting agent for drug in the present invention is capable of imparting a sustained-release ability to a drug, and contains a polypeptide represented by Ac-(Arg-Ala-Asp-Ala)$_4$-NH$_2$ and an organic solvent. The organic solvent is at least one organic solvent selected from the group consisting of polyethylene glycol, dimethyl sulfoxide, glycofurol, and N-methylpyrrolidone. As details of ingredients and additional additives, those described for the foregoing pharmaceutical composition can be applied to this sustained-release ability imparting agent without any change. For example, the details of the polypeptide and the solvent for are the same as those described above, and the sustained-release ability imparting agent is also the same as the above-explained pharmaceutical composition in that the aforementioned additives can be added. As for a ratio of the sustained-release ability imparting agent:the drug in the present invention, for example, an appropriate mass ratio is 0.01:99.99 to 30:70, preferably 0.1:99.9 to 25:75, more preferably 0.5:99.5 to 20:80, even more preferably 1:99 to 15:85, or particularly preferably 1:99 to 12:88.

Hereinafter, preparation examples and their test results will be demonstrated, but these are intended to facilitate better understanding of the present invention, and are not intended to limit the scope of the present invention.

EXAMPLES

Preparation Examples

Hereinafter, typical preparation examples of the present invention will be presented. In the following preparation examples, a content of each ingredient is a content of the ingredient in 100 mL of the composition.

| Preparation Example 1 | |
|---|---|
| Drug | 4 g |
| Polypeptide A | 0.1 g |
| PEG 400/Water (volume ratio 9/1) | Proper Quantity |
| Preparation Example 2 | |
| Drug | 4 g |
| Polypeptide A | 0.5 g |
| PEG 400/Water (volume ratio 9/1) | Proper Quantity |
| Preparation Example 3 | |
| Drug | 4 g |
| Polypeptide A | 0.1 g |
| PEG 400/Water (volume ratio 8/2) | Proper Quantity |
| Preparation Example 4 | |
| Drug | 4 g |
| Polypeptide A | 0.5 g |

-continued

| Preparation Example 1 | |
|---|---|
| PEG 400/Water (volume ratio 8/2) | Proper Quantity |
| Preparation Example 5 | |
| Drug | 4 g |
| Polypeptide A | 0.1 g |
| DMSO | Proper Quantity |
| Preparation Example 6 | |
| Drug | 4 g |
| Polypeptide A | 0.5 g |
| DMSO | Proper Quantity |

Note that a desired composition can be obtained by adjusting the contents of the drug, the polypeptide A, and the solvent in any of the preparation examples 1 to 6 as appropriate.

1. Dissolution Performance Evaluation Test

Drug dissolving abilities of various solutions were examined.

1-1. Test Method

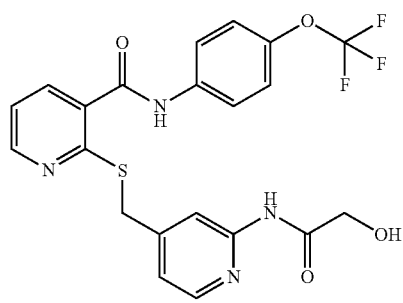

(2)

The compound represented by the above formula (2) (2-[[[2-[(hydroxyacetyl)amino]-4-pyridinyl]methyl]thio]-N-[4-(trifluoromethoxy)phenyl]-3-pyridinecarboxamide, hereinafter also referred to as the drug A; prepared in accordance with the method described in the specification of US Patent Application Publication No. 2007/0149574) was added to each solvent (total 1 mL) out of various solvents of DMSO (GAYLORD), PEG 400 (Nacalai Tesque), and water, and was stirred at room temperature (25° C.) overnight (for 8 hours). Then, the properties of the resultant solvents were visually checked.

1-2. Test Results and Consideration

Table 1 presents test results. As can be understood from Table 1, the solution containing DMSO or PEG 400 can dissolve the drug which cannot be dissolved in water.

TABLE 1

| | Test 1 | Test 2 | Test 3 | Test 4 | Test 5 | Test 6 | Test 7 |
|---|---|---|---|---|---|---|---|
| Drug A | 20 mg | 60 mg | 60 mg | 25 mg | 25 mg | 25 mg | 25 mg |
| DMSO | 0.9 mL | 0.9 mL | — | — | — | — | — |
| PEG 400 | — | — | — | 1 mL | 0.9 mL | 0.8 mL | — |
| Water | 0.1 mL | 0.1 mL | 1 mL | — | 0.1 mL | 0.2 mL | 1 mL |
| Property | Solution | Solution | Suspension | Solution | Solution | Solution | Suspension |

2. Depot Formation Evaluation Test (1)

Depot (deposited mass) formations of various kinds of gelatinizers were examined.

2-1. Test Method

Compositions 1 to 6 were prepared by blending each of various kinds of gelatinizers to a solvent of DMSO/water (volume ratio of 9:1) such that the gelatinizer is contained at 0.1% (w/v) (0.1% by mass of the gelatinizer is contained per 100 mL of the solution of DMSO/water). Then, calcium chloride dihydrate and magnesium chloride hexahydrate were dissolved in Dulbecco's phosphate buffered saline (−) (Product No. D-5652 manufactured by Sigma-Aldrich) to prepare Dulbecco's phosphate buffered saline (+). 0.005 mL of each of the compositions was added to 1 mL of the Dulbecco's phosphate buffered saline (+), and the formation of a depot was visually checked. The formation of a depot was evaluated in such a way that the depot is determined as formed if a mass formed of the composition deposited is observed.

2-2. Test Results and Consideration

Table 2 presents test results. As can be understood from Table 2, only the polypeptide A formed a depot in the solution of DMSO/water at the volume ratio (9:1) among the various kinds of gelatinizers. This demonstrated that the sustained-release ability imparting agent in the present invention is capable of sustained-releasing a drug by forming a depot when administered into the body together with the drug.

TABLE 2

|  | Ex. 1 | Comp. Ex. 1 | Comp. Ex. 2 | Comp. Ex. 3 | Comp. Ex. 4 | Comp. Ex. 5 |
|---|---|---|---|---|---|---|
| Gelatinizer (0.1% W/V) | Polypeptide A | Polyethylene Glycol 4000 | Polycarbophil | Polyvinyl Alcohol | Sodium Alginate | Chitosan |
| Composition Properties | Clear Colorless Solution | Clear Colorless Solution | Clear Colorless Solution | Clear Colorless Solution | White Yellow Suspension | White Yellow Suspension |
| Depot Formation | ○ | x | x | x | x | x |

○ Depot was formed.
x No Depot was formed.

3. Depot Formation Evaluation Test (2)

Solvents of the polypeptide A were examined.

3-1. Test Method

Compositions 2 to 6 and Comparative Examples 6 and 7 were prepared by adding 0.01 mL of an aqueous solution of the polypeptide A at 1% (w/v) (containing 1% by mass of the polypeptide A per 100 mL of water) to 0.09 mL of each of various solvents, followed by stirring. 0.005 mL of each of the compositions was administered to 1 mL of the Dulbecco's phosphate buffered saline (+), and the formation of a depot was visually checked.

3-2. Test Results and Consideration

Table 3 presents test results. As can be understood from Table 3, the polypeptide A formed a depot in any of the cases where DMSO, PEG 200, PEG 400, glycofurol (a mixture having mainly 1 to 4 repeating units) and N-methylpyrrolidone were used as the solvents. On the other hand, in the cases where the ethanol and N,N-dimethylacetamide were used as the solvents, the polypeptide A did not form a depot. This demonstrated that the sustained-release ability imparting agent in the present invention is capable of sustained-releasing a drug by forming a depot when administered into the body together with the drug.

TABLE 3

|  | Ex. 2 | Ex. 3 | Ex. 4 | Ex. 5 | Ex. 6 | Comp. Ex. 6 | Comp. Ex. 7 |
|---|---|---|---|---|---|---|---|
| Solvent | DMSO | PEG 200 | PEG 400 | Glycofurol | N-methylpyrrolidone | Ethanol | N,N-Dimethylacetamide |
| Composition Properties | Clear Colorless Solution | Clear Colorless Solution | Clear Colorless Solution | Clear Colorless Solution | Clear Colorless Solution | Heterogeneous Liquid | Clear Colorless Solution |
| Depot Formation | ○ | ○ | ○ | ○ | ○ | x | x |

○ Depot was formed.
x No Depot was formed.

4. Sustained-Release Ability Evaluation Test

The sustained-release ability of a drug from a depot was examined.

4-1. Preparation of Composition to be Tested

A composition A was obtained by adding 0.25 g of the drug A to 8 mL of PEG 400 (Nacalai Tesque), and dissolving the drug A by stirring.

A composition B was obtained by adding 0.4 mL of water to 1.6 mL of the composition A and dissolving the composition A.

A composition C was obtained by putting 1 mL of an aqueous solution of the polypeptide A at 1% (w/v) (containing 1% by mass of the polypeptide A per 100 mL of water) into a standard bottle, freeze-drying the solution at −35 to 30° C., and then adding 1.6 mL of the composition A and 0.4 mL of water to the resultant substance, followed by mixing by stirring.

A composition D was obtained by adding 0.7 mL of the composition B to 0.7 mL of the composition C, followed by mixing by stirring.

A composition E was obtained by adding 0.8 mL of the composition B to 0.2 mL of the composition C, followed by mixing by stirring.

A composition F was obtained by adding 25 mg of the drug A to 1 mL of PEG 400 (Nacalai Tesque), and dissolving the drug A by stirring.

4-2. Test Method

Water was added to 10 g of polyoxyl 40 stearate (Nikko Chemicals) and 9.6 g of Dulbecco's phosphate buffered saline (Sigma Aldrich) to prepare a solvent in the total amount of 1 L (release solvent).

20 mL of the release solvent heated to 37° C. was put into each standard bottle, and 0.01 mL of the test solution of each of the compositions C to F test solutions was inputted to the standard bottle, followed by stirring at 37° C. and 86 rpm for 6 days. The amount of the drug A released into the release solvent was quantified using high performance liquid chromatography (HPLC), and the release rate (%) was calculated. The release rate was calculated based on the following formula.

Release Rate (%)=[Amount of Drug Released (mass)]/[Initial Amount of Drug (Dosage) (mass)]×100

In the case of calculating a release rate after 1 day, for example, in accordance with the above formula where Day 0 denotes a day when the test solution of each of the compositions is inputted to the release solvent and after 1 day means after the passage of 1 day (24 hours) from the input, [Initial Amount of Drug (Dosage) (mass)] is an amount of the drug inputted at the time of drug input (on Day 0), and "Amount of Drug Released (mass)" is an amount of the drug released after the passage of 1 day.

4-3. Test Results and Consideration

Table 4 presents test results. As can be understood from Table 4, after being inputted to the release solvents, the compositions C to E formed depots and sustained-released the drug A over 1 to 6 days.

TABLE 4

|  |  | Ex. 7 | Ex. 8 | Ex.9 | Comp. Ex. 8 |
|---|---|---|---|---|---|
| Solution |  | Comp. C | Comp. D | Comp. E | Comp. F |
| Drug A (% w/v) |  | 2.5 | 2.5 | 2.5 | 2.5 |
| Polypeptide A (% w/v) |  | 0.5 | 0.25 | 0.1 | — |
| PEG 400/Water (v/v) |  | 80/20 | 80/20 | 80/20 | 100/0 |
| Depot Formation |  | ○ | ○ | ○ | × |
| Release Rate (%) | After 1 Day | 42.7 | 43.5 | 81.7 | 103.1 |
|  | After 6 Days | 88.1 | 88.9 | 100.1 | — |

○: Depot was formed.
×: No Depot was formed.

As described above, it has been suggested that the pharmaceutical composition in the present invention dissolves a drug therein and sustained-releases the drug by forming a deport after administration into the body.

[SEQ ID Table Free Text]

(SEQ ID NO: 1) It is sold as PuraMatrix (registered trademark) by 3-D Matrix, Ltd.

The invention claimed is:

1. A pharmaceutical composition comprising:
   a drug;
   a polypeptide represented by Ac-(Arg-Ala-Asp-Ala)$_4$-NH$_2$; and
   an organic solvent, wherein:
   the organic solvent is at least one organic solvent selected from the group consisting of polyethylene glycol, dimethyl sulfoxide, glycofurol, and N-methylpyrrolidone.

2. The pharmaceutical composition according to claim 1, further comprising water.

3. The pharmaceutical composition according to claim 2, wherein a volume ratio of the organic solvent to the water is 99:1 to 60:40.

4. The pharmaceutical composition according to claim 1, wherein:
   the organic solvent is polyethylene glycol, and
   the polyethylene glycol has a mean molecular weight within a range of 90 to 2200.

5. The pharmaceutical composition according to claim 1, wherein:
   the organic solvent is polyethylene glycol, and
   the polyethylene glycol is PEG 400.

6. The pharmaceutical composition according to claim 1, wherein a content of the drug is 0.01 to 30% (w/v).

7. The pharmaceutical composition according to claim 1, wherein a content of the polypeptide represented by Ac-(Arg-Ala-Asp-Ala)$_4$-NH$_2$ is 0.001 to 5% (w/v).

8. The pharmaceutical composition according to claim 1, wherein a content of the organic solvent is 70 to 99.99% (w/w).

9. The pharmaceutical composition according to claim 1, wherein the pharmaceutical composition consisting substantially only of the drug, the polypeptide represented by Ac-(Arg-Ala-Asp-Ala)$_4$-NH$_2$, the polyethylene glycol, and the water.

10. The pharmaceutical composition according to claim 1, wherein the pharmaceutical composition consisting substantially only of the drug, the polypeptide represented by Ac-(Arg-Ala-Asp-Ala)$_4$-NH$_2$, and the dimethyl sulfoxide.

11. The pharmaceutical composition according to claim 1, wherein:
    the drug is a compound or a salt thereof, the compound represented by formula (1):

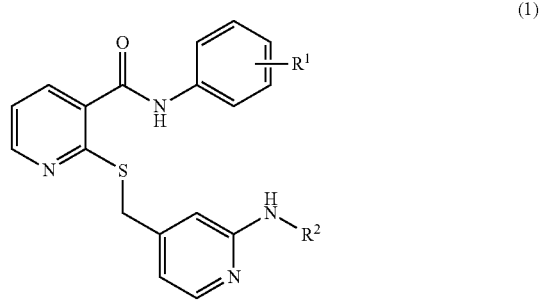

(1)

wherein
- R¹ represents a hydrogen atom, a halogen atom, a hydroxyl group, a $C_{1-6}$ alkyl group, a $C_{1-6}$ alkyl group substituted with one or more halogen atoms, a $C_{1-6}$ alkoxy group, or $C_{1-6}$ alkoxy group substituted with one or more halogen atoms; and
- R² represents a hydrogen atom, $C_{1-6}$ alkyl group, a $C_{1-6}$ alkylcarbonyl group, or a $C_{1-6}$ alkylcarbonyl group substituted with one or more hydroxyl groups.

12. The pharmaceutical composition according to claim 1, wherein the drug is 2-[[[2-[(hydroxyacetyl)amino]-4-pyridinyl]methyl]thio]-N-[4-(trifluoromethoxy)phenyl]-3-pyridinecarboxamide or a salt thereof.

13. The pharmaceutical composition according to claim 1, wherein the pharmaceutical composition is for preventing or treating an eye disease.

14. The pharmaceutical composition according to claim 13, wherein the pharmaceutical composition is for intravitreal or intracameral administration.

15. The pharmaceutical composition according to claim 13, wherein the pharmaceutical composition is for sustained-releasing the drug.

16. A sustained-release ability imparting agent for drug comprising:
- a polypeptide represented by Ac-(Arg-Ala-Asp-Ala)₄-NH₂; and
- an organic solvent, wherein
- the organic solvent is at least one organic solvent selected from the group consisting of polyethylene glycol, dimethyl sulfoxide, glycofurol, and N-methylpyrrolidone.

17. A method of imparting a sustained-release ability to a drug, the method comprising adding a polypeptide represented by Ac-(Arg-Ala-Asp-Ala)₄-NH₂ and an organic solvent to a drug, wherein:
- the organic solvent is at least one organic solvent selected from the group consisting of polyethylene glycol, dimethyl sulfoxide, glycofurol, and N-methylpyrrolidone.

18. A method of preventing or treating an eye disease comprising administering the pharmaceutical composition according to claim 4.

19. The sustained-release ability imparting agent according to claim 16, further comprising water.

20. The method of imparting a sustained-release ability to a drug according to claim 17, wherein: the organic solvent is polyethylene glycol, and the polyethylene glycol has a mean molecular weight within a range of 90 to 2200.

* * * * *